(12) United States Patent
Mori et al.

(10) Patent No.: US 10,413,176 B2
(45) Date of Patent: Sep. 17, 2019

(54) INATTENTION MEASUREMENT DEVICE, SYSTEM, AND METHOD

(71) Applicant: NATIONAL UNIVERSITY CORPORATION HAMAMATSU UNIVERSITY SCHOOL OF MEDICINE, Hamamatsu-shi, Shizuoka (JP)

(72) Inventors: Norio Mori, Hamamatsu (JP); Katsuaki Suzuki, Hamamatsu (JP); Kenji Tsuchiya, Hamamatsu (JP); Chie Shimmura, Hamamatsu (JP)

(73) Assignee: NATIONAL UNIVERSITY CORPORATION HAMAMATSU UNIVERSITY SCHOOL OF MEDICINE, Hamamatsu-Shi, Shizuoka (JP)

( * ) Notice: Subject to any disclaimer, the term of this patent is extended or adjusted under 35 U.S.C. 154(b) by 230 days.

(21) Appl. No.: 15/515,223

(22) PCT Filed: Sep. 30, 2015

(86) PCT No.: PCT/JP2015/077803
§ 371 (c)(1),
(2) Date: Mar. 29, 2017

(87) PCT Pub. No.: WO2016/052646
PCT Pub. Date: Apr. 7, 2016

(65) Prior Publication Data
US 2017/0224210 A1    Aug. 10, 2017

(30) Foreign Application Priority Data

Sep. 30, 2014  (JP) ................ 2014-201029

(51) Int. Cl.
*A61B 3/113* (2006.01)
*A61B 10/00* (2006.01)
(Continued)

(52) U.S. Cl.
CPC .............. *A61B 3/113* (2013.01); *A61B 5/163* (2017.08); *A61B 5/168* (2013.01); *A61B 5/7275* (2013.01);
(Continued)

(58) Field of Classification Search
CPC ........ A61B 5/168; A61B 3/113; A61B 5/7275
See application file for complete search history.

(56) References Cited

U.S. PATENT DOCUMENTS

| 8,950,864 B1* | 2/2015 | Massengill | .......... A61B 5/4064 351/209 |
| 2010/0092929 A1* | 4/2010 | Hallowell | ................ G09B 5/06 434/167 |

(Continued)

FOREIGN PATENT DOCUMENTS

| JP | 2005-287571 A | 10/2005 |
| JP | 2013-052116 A | 3/2013 |

(Continued)

OTHER PUBLICATIONS

Notification of Transmittal of Translation of the International Preliminary Report on Patentability (Form PCT/IB/338) and Translation of International Preliminary Report on Patentability (Chapter II of the Patent Cooperation Treaty) (Form PCT/IPEA/409) for International Application No. PCT/JP2015/077803 dated Apr. 6, 2017 (5 pages).

(Continued)

*Primary Examiner* — Eric F Winakur
(74) *Attorney, Agent, or Firm* — Withrow & Terranova, P.L.L.C.; Vincent K. Gustafson

(57) ABSTRACT

An inattention measurement device, system, and method wherein an index value indicating an inattention level of a (Continued)

subject is calculated based on information relating to a history of a gazing point of a subject when presented with a task of searching for a prescribed target.

20 Claims, 11 Drawing Sheets

(51) Int. Cl.
*A61B 5/16* (2006.01)
*A61B 5/00* (2006.01)
*G06K 9/00* (2006.01)

(52) U.S. Cl.
CPC .......... *A61B 10/00* (2013.01); *G06K 9/00604* (2013.01); *G06K 9/00617* (2013.01)

(56) References Cited

U.S. PATENT DOCUMENTS

| | | |
|---|---|---|
| 2012/0271194 A1 | 10/2012 | MacLullich et al. |
| 2014/0213930 A1 | 7/2014 | Mori et al. |
| 2015/0050628 A1 | 2/2015 | Mori et al. |
| 2015/0112224 A1 | 4/2015 | Super |
| 2017/0188930 A1 | 7/2017 | Lahvis |

FOREIGN PATENT DOCUMENTS

| | | |
|---|---|---|
| JP | 2013-223713 A | 10/2013 |
| JP | 2014-071779 A | 4/2014 |
| JP | 2015-043963 A | 3/2015 |
| WO | 2011042703 A1 | 4/2011 |
| WO | 2013159841 A1 | 10/2013 |
| WO | 2016040673 A2 | 3/2016 |

OTHER PUBLICATIONS

Extended European Search Report for European Patent Application No. 15847961.8, dated Mar. 21, 2018, 7 pages.
International Search Report (Form PCT/ISA/210) for International Application No. PCT/JP2015/077803 dated Dec. 22, 2015 (3 pages including English translation).
Treisman, Anne M. and Gelade, Garry, "A Feature-Integration Theory of Attention," Cognitive Psychology 12, pp. 97-136 (1980).
Hazell, Philip L., et al., "Effortful and Automatic Information Processing in Boys with ADHD and Specific Learning Disorders," J. Child Psychol. Psychiat., vol. 40, No. 2, pp. 275-286, Cambridge University Press (1999).
Hibi, Yuko, et al., "Visual search performance in children with attention-deficit/hyperactivity disorder, autism spectrum disorder, and mental retardation," Human Developmental Research, vol. 26, pp. 121-130 (2012) (includes English abstract at pp. 121-122).
Reeve, Whitney V. and Schandler, Steven L., "Frontal Lobe Functioning in Adolescents with Attention Deficit Hyperactivity Disorder," Adolescence, vol. 36, No. 144, pp. 749-765, Libra Publishers, Inc. (2001).
O'Riordan, Michelle A., et al., "Superior Visual Search in Autism," Journal of Experimental Psychology: Human Perception and Performance, vol. 27, No. 3, pp. 719-730 (2001).
Plaisted, Kate, et al., "Towards an understanding of the mechanisms of weak central coherence effects: experiments in visual configural learning and auditory perception," Configural learning and psychoacoustics, Phil. Trans. R. Soc. Lond. B, 358, 375-386, The Royal Society (2003).

\* cited by examiner

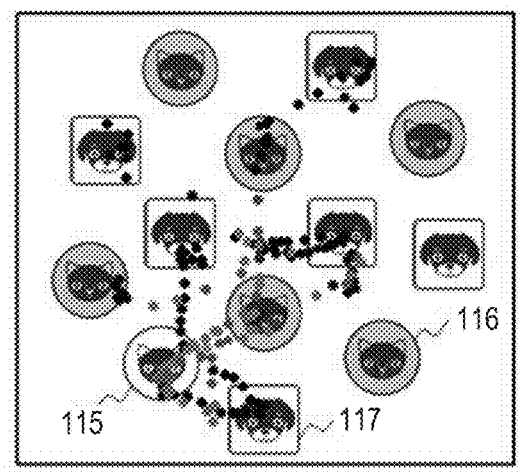 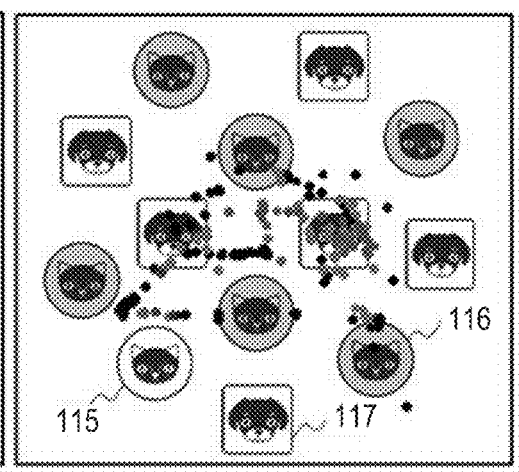

FIG. 6

| No. | Title | Type | START TIME | MEASURE-MENT TIME | DATA RATE | REACTION TIME 1 | REACTION TIME 2 | MOVE-MENT RATE 1 | MOVE-MENT RATE 2 | RATIO OUTSIDE AREA | NUMBER OF SCAN OBJECT 1 | NUMBER OF SCAN OBJECT 2 |
|---|---|---|---|---|---|---|---|---|---|---|---|---|
| 1 | FEATURE 1 | B | 49.00 | 4.50 | 1.000 | 0.820 | 1.200 | 253.809 | 216.246 | 0.569 | 5 | 12 |
| 2 | FEATURE 2 | B | 53.50 | 2.00 | 1.000 | 0.440 | 0.780 | 323.884 | 0.000 | 0.780 | 1 | 5 |
| 3 | CONJUNCTION 1 | C | 57.50 | 4.50 | 1.000 | 3.160 | 3.260 | 362.422 | 187.500 | 0.596 | 4 | 14 |
| 4 | CONJUNCTION 2 | C | 62.00 | 2.00 | 1.000 | 0.480 | 0.560 | 304.226 | 283.437 | 0.270 | 2 | 11 |
| 5 | FEATURE 3 | B | 66.00 | 4.50 | 0.831 | 0.680 | 0.720 | 604.418 | 162.145 | 0.307 | 5 | 10 |
| 6 | FEATURE 4 | B | 70.50 | 2.00 | 0.890 | 0.560 | 0.600 | 1336.120 | 186.404 | 0.240 | 4 | 5 |
| 7 | CONJUNCTION 3 | C | 74.50 | 4.50 | 1.000 | 1.460 | 1.500 | 353.720 | 268.695 | 0.422 | 7 | 12 |
| 8 | CONJUNCTION 4 | C | 79.00 | 2.00 | 1.000 | 0.460 | 0.500 | 274.139 | 207.670 | 0.390 | 4 | 5 |
| 9 | FEATURE 5 | B | 83.00 | 4.50 | 0.920 | 0.820 | 0.860 | 306.696 | 117.799 | 0.596 | 2 | 12 |
| 10 | FEATURE 6 | B | 87.50 | 2.00 | 0.480 | 0.960 | 1.000 | 1537.007 | 0.000 | 0.270 | 1 | 3 |
| 11 | CONJUNCTION 5 | C | 91.50 | 4.50 | 0.733 | 2.720 | 2.760 | 679.896 | 266.407 | 0.311 | 8 | 15 |
| 12 | CONJUNCTION 6 | C | 96.00 | 2.00 | 0.000 | 0.000 | 0.000 | 0.000 | 0.000 | 0.000 | 0 | 0 |

INATTENTION MEASUREMENT DEVICE, SYSTEM, AND METHOD

CROSS-REFERENCE TO RELATED APPLICATIONS

This application is a 35 U.S.C. § 371 national phase filing of International Application No. PCT/JP2015/077803 filed on Sep. 30, 2015, and claims the benefit of Japanese Patent Application No. 2014-201029 filed on Sep. 30, 2014 with the Japan Patent Office. The entire disclosures of International Application No. PCT/JP2015/077803 and Japanese Patent Application No. 2014-201029 are hereby incorporated by reference herein in their respective entireties.

TECHNICAL FIELD

The present invention relates to an inattention measurement device, system, and method, program, and recording medium.

BACKGROUND ART

Psychiatric human "inattention" brings about various obstacles to human's daily life. Here, another name "attention deficit" also exists for "inattention", which is also referred to as "decline in attentional function" in cognitive science.

There are multiple neuropsychiatric diseases of which main symptoms are inattention. Among them, attention deficit/hyperactive disorder (hereinafter referred to as "ADHD") is a neuropsychiatric disease affecting many humans regardless of age. According to previous studies, a prevalence rate of ADHD is said to be 5% or more. ADHD is classified as "predominantly inattentive type" and "predominantly hyperactive-impulsive type", and in particular, the former is extremely difficult to find and diagnose. Nonetheless, considerable difficulties arise in social adaptation such as school and work depending on the symptoms. Thus, great expectations are gathered throughout the world for attempts to improve social outcome of children and persons with ADHD by early detection of inattention as well as by early diagnosis of ADHD, for example, by the National Institute of Mental Health (NIMH), etc.

In general, early detection and early diagnosis of ADHD is considered to be possible at the age of 3 to 6 years old. Diagnosis of ADHD, including attention deficit, is carried out by experienced pediatric neurologists, pediatric psychiatrists, or clinical psychologists, or by rating scales (questionnaires).

In the field of experimental psychology, comparative studies between ADHD children/persons and typically developing children/persons have been conducted using visual stimuli including visual search, in particular, feature search and conjunction search. Then, it has been reported that there is a delay specific to a child/person of ADHD, that is, a delay in reaction time until a prespecified target is found out (see, for example, Non-Patent Documents 1 to 3). Also, a delay specific to a child/person of ADHD has been reported similarly in Erichsen's Franker task and Stroop task which are tasks (visual stimuli) causing competition (for example, see Non-Patent Document 4).

In addition, a diagnosis support device for diagnosing autism using a device for measuring a gazing point of a subject is disclosed (Patent Documents 1 to 3).

PRIOR ART DOCUMENTS

Patent Documents

Patent Document 1: Japanese Unexamined Patent Publication No. 2014-71779
Patent Document 2: Japanese Unexamined Patent Application Publication No. 2013-223713
Patent Document 3: Japanese Unexamined Patent Application Publication No. 2013-52116

Non Patent Documents

Non-Patent Document 1: Treisman, A and Gelade, G (1980) Cognitive Psychology, 12, 97-136.
Non-Patent Document 2: Hazel, P L et al (1999) Journal of Child Psychology and Psychiatry, 40 (2), 275-286.
Non-Patent Document 3: Yuko Hibi et al. (2012) Human Developmental Research, 26, 121-130.
Non-Patent Document 4: Reeve, W V and Schandler, S L (2001) Adolescence 36 (144) 11-17.

SUMMARY OF THE INVENTION

Problems to be Solved by the Invention

In the diagnosis of ADHD by conventional experts, there is a difference in evaluation of each evaluator, and objective evaluation is difficult. Also, there has been no widely used objective measurement method of inattention based on physical findings.

In the tasks disclosed in Non-Patent Documents 1 to 4, a subject has to satisfy the following conditions:
  1) understands procedures of how to execute tasks explained in advance,
  2) presses a button without delay when searching for a target in tasks using visual search, and
  3) distinguishes and presses multiple buttons and reads characters in tasks causing competition.

In addition, the results of previous studies using visual search do not necessarily match. Therefore, there is a high hurdle to realize early detection and diagnosis of ADHD, especially of low age group, using these tasks. In addition, other psychiatric disorders such as intellectual disability may accompany ADHD. Such subjects have further difficulty in accomplishing these tasks. Therefore, these tasks have never been applied to early detection and early diagnosis of ADHD in clinical practice.

In one aspect of the present disclosure, it is desirable to be able to provide a method, device, system, etc. for measuring inattention in a simple, accurate and objective manner without restriction by age and symptoms of a subject.

Means for Solving the Problems

An inattention measurement device according to a first aspect of the present disclosure calculates an index value indicating an inattention level of a subject based on information relating to a history of a gazing point of the subject when presented with a task of searching for a predetermined target. An example inattention measurement device comprises an acquisition unit that acquires information relating to a history of a gazing point of a subject when presented with a task of searching for a predetermined target; and a calculation unit that calculates an index value indicating an inattention level of the subject based on the information acquired by the acquisition unit. The acquisition unit can be configured to acquire information relating to the history of the gazing point of the subject, for example, by measurement, from another device, or by reading from a storage device.

An inattention measurement system according to a second aspect of the present disclosure comprises at least a gazing point measurement device that measures information relating to a history of a gazing point of a subject when presented with a task of searching for a predetermined target, and an inattention measurement device that calculates an index value indicating an inattention level of the subject based on the information relating to the history of the gazing point measured by the gazing point measurement device.

A method of operating an inattention measurement device or a method of measuring inattention level according to a third aspect of the present disclosure comprises: calculating an index value indicating an inattention level of a subject, based on information relating to a history of a gazing point of the subject when presented with a task of searching for a predetermined target, and comparing the calculated index value indicating the inattention level of the subject with one or more preset thresholds.

A program according to a fourth aspect of the present disclosure causes a computer to perform calculation of an index value indicating an inattention level of a subject based on information relating to a history of a gazing point of the subject when presented with a task of searching for a predetermined target. An example program causes a computer to perform acquisition of information relating to a history of a gazing point of a subject when presented with a task of searching for a predetermined target, and calculation of an index value indicating an inattention level of the subject based on the information relating to the history of the gazing point of the subject. The acquisition can include acquiring information relating to the history of the gazing point of the subject, for example, by measurement, from another device, or by reading from a storage device. A method of measuring inattention level may be provided, the method comprising: acquiring information relating to a history of a gazing point of a subject when presented with a task of searching for a predetermined target; and calculating an index value indicating an inattention level of the subject based on the information relating to the history of the gazing point of the subject.

A computer-readable recording medium according to a fifth aspect of the present disclosure records a program according to the fourth aspect.

According to one aspect of the present disclosure, measurement of inattention can be easily, accurately and objectively conducted without being restricted by age and symptoms of a subject. According to one aspect of the disclosure, a full scale screening for early detection of inattention can be performed on a large scale, in some cases.

BRIEF DESCRIPTION OF THE DRAWINGS

FIGS. 5A and 5B are diagrams respectively showing an example of gazing point positions of a typical developing child and an ADHD child.

FIG. 6 is a diagram showing an example of a result display screen.

EXPLANATION OF REFERENCE NUMERALS

Figure 1:
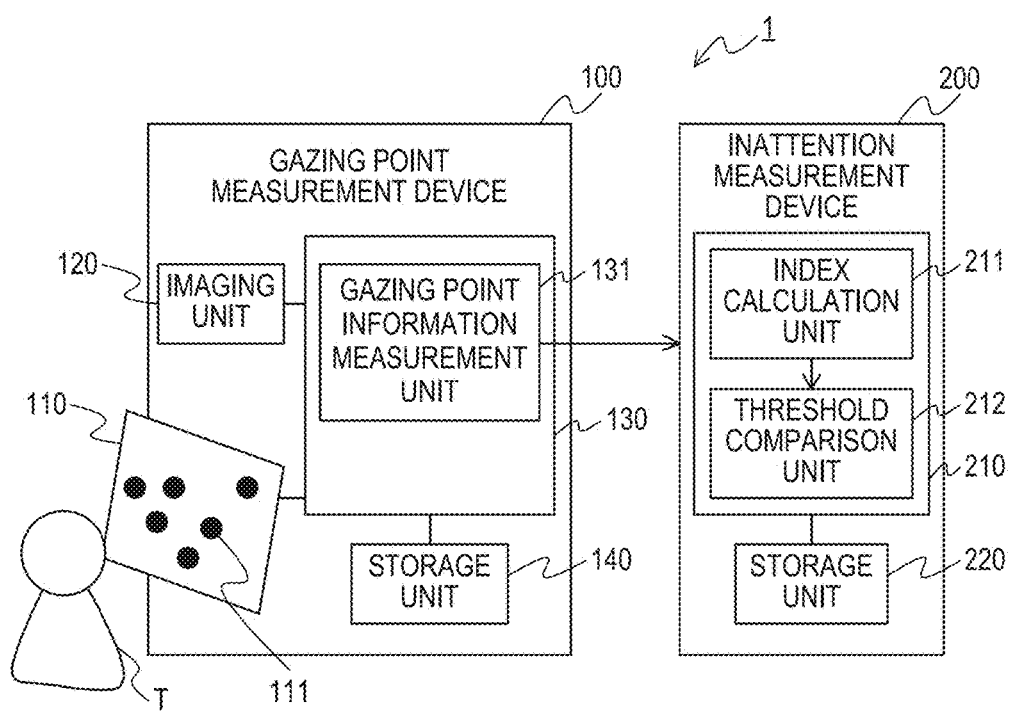
FIG. 1 is a diagram showing a schematic configuration of an inattention measurement system.

1 . . . inattention measurement system, 100, 100' . . . gazing point measurement device, 110 . . . display unit, 111 . . . visual stimulus, 112, 115 . . . target, 113, 116 . . . one example of first distractor, 114, 117 . . . one example of second distractor, 120 . . . imaging unit, 130 . . . control unit, 131 . . . gazing point information measurement unit, 140 . . . storage unit (gazing point measurement device), 200, 200' . . . inattention measurement device, 210 . . . operation unit, 211 . . . index value calculation unit, 212 . . . threshold comparison unit, 220 . . . storage unit (inattention measurement device), 313 . . . display unit of value of each item, 314 . . . search time (sec), 315 . . . movement distance (pixel), 316 . . . number (total number) of searches for distractor, 317 . . . display unit of information relating to subject

MODE FOR CARRYING OUT THE INVENTION

Hereinafter, an embodiment of the present disclosure will be described. The present disclosure is not limited to this embodiment. In the following description, the same elements are denoted by the same reference numerals, and duplicate description is omitted.

FIG. 1 is a diagram showing a schematic configuration of an inattention measurement system 1 of the present embodiment. The inattention measurement system 1 comprises a gazing point measurement device 100 and an inattention measurement device 200. In the inattention measurement system 1, information relating to a history of a gazing point of a subject T can be measured by the gazing point measurement device 100 and an index value indicating inattention level can be calculated by the inattention measurement device 200 based on the measured information.

First, the gazing point measurement device 100 of the present embodiment will be described.

The gazing point measurement device 100 according to the present embodiment comprises a display unit 110, an imaging unit 120 that captures an image of the eye of the subject T, and a gazing point information measurement unit 131. The gazing point measurement device 100 can present a visual stimulus 111 to the subject T by the display unit 110 and acquire information relating to the gazing point by using the captured image of the eye of the subject T.

The display unit 110 displays the visual stimulus 111 to the subject T. For the display unit 110, for example, a commercially available display can be used. The commercially available display can include a liquid crystal display, a CRT, a projector, or the like. The size and shape of a display screen is not particularly limited. A stereoscopic display or the like which can produce a sense of depth on a display screen may be used.

The visual stimulus 111 may be any stimulus as long as it allows measurement of information relating to a history of a gazing point when presented to a subject and can be appropriately selected according to symptoms of the subject. The visual stimulus 111 can include a task of causing a subject to search for a specific target (visual stimulus). The specific object searched by the subject is called a target.

The target is a specific object to be searched by the subject. The target can be defined, for example, by combining visually distinguishable features such as shape, color, brightness, movement and the like. The shape of the target includes, for example, one or more of a specific graphic, character, symbol, and three-dimensional shape.

The task of searching the target is referred to as visual search. The visual search may include a target and a distractor. The distractor is a visual stimulus other than the target, and has one or more features different from the target. The visual stimulus 111 can also include a picture composed of still image and animation. For the target and/or distractor, a graphic, letter, illustration, person, landscape, etc. may be used.

Upon presenting visual search 111, the target 112 may be presented to a subject in advance and the subject may be instructed to search for the target 112. After presenting the target 112, the display unit 110 can provide a visual search including only a distractor and not including the target 112. The display unit 110 may not present the target 112 to the subject in advance, and may provide a visual search so that the subject spontaneously directs attention to the target 112.

For example, as shown in FIGS. 3A to 3F, when a subject of low age group is targeted, a character such as a person, animal or plant may be used as a target 115 and/or distractors 116 and 117. Thereby, the subject's attention can be directed to the target 115 and/or the distractors 116, 117. In addition, it becomes easy to explain the target to be searched in advance to the subject.

Figure 2A:
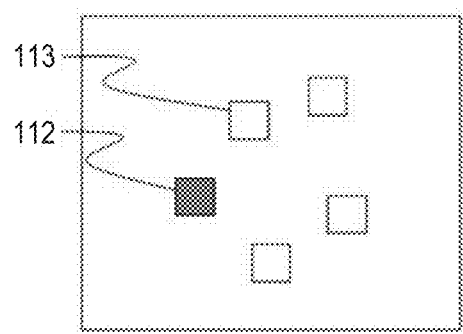
FIGS. 2A to 2D are diagrams each showing an example of feature search and conjunction search.
Figure 2C:
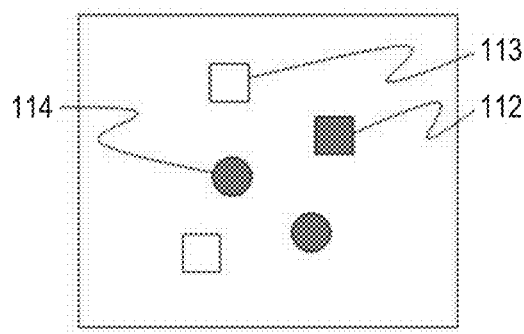
Figure 2B:
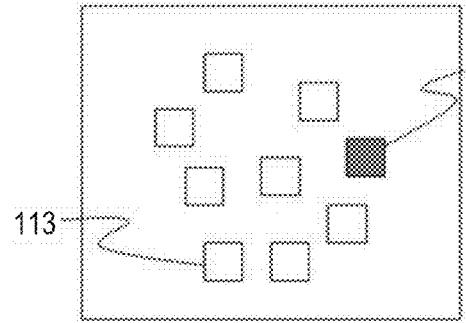
Figure 2D:
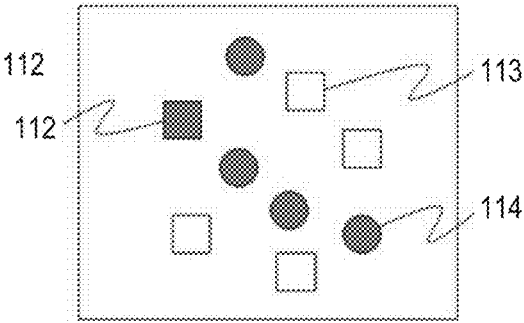

The visual search includes, for example, as shown in FIGS. 2A to 2D, feature searches (FIGS. 2A and 2B) and conjunction searches (FIGS. 2C and 2D).

FIGS. 2A and 2B show examples of feature searches. The feature search is a task in which a target different from a distractor is defined by a single feature that is visually distinguishable (for example, a single shape, color or movement, etc.) (see Non-Patent Document 1). In FIGS. 2A and 2B, the target 112 is indicated by a square of first color (e.g., red) and the distractor 113 by a square of second color (e.g., blue). Normally, if the target has a single feature clearly distinct from the distractor, the target can be found with a nearly constant search time regardless of the number of distractors.

FIGS. 2C and 2D are diagrams showing examples of conjunction searches. The conjunction search is a task in which a target different from a distractor is defined by a combination of two or more features (for example, shape and color) (see Non-Patent Document 1). For example, the conjunction search may be performed by combining two or more types of distractors (for example, first and second distractors, etc.), such as a distractor that differs only in color from the target and a distractor that differs only in size from the target.

FIGS. 2C and 2D show that the feature stimulus 112 is represented by a square of first color (e.g., red), a first distractor is represented by a square 113 of second color (e.g., blue), and a second distractor is represented by a circle 114 of first color. Normally, for conjunction searches, sequential processing of examining a target by comparison with distractors is performed, so that search time to find the target increases as the number of distractors increases.

As shown in an example to be described later, in a case of a ADHD child/person, a time until a gazing point is detected in a target area (search time) becomes longer as compared with that of a typically developing child/person, in both feature search and conjunction search. Therefore, use of feature search and/or conjunction search as the visual search makes measurement of inattention level easier.

In a conjunction search, adjusting the number of distractors allows adjustment of difficulty level of a task and appropriate setting of a task according to age and symptoms of a subject. Therefore, use of a conjunction search as the visual stimulus allows measurement of a wide range of levels of inattention from mild to severe.

In a conventional method in which a search time for a target is measured by a time until a subject presses a button (reaction time), there is a possibility that the measured value does not indicate accurate reaction time. For example, feature search exhibits a tendency of a shorter search time compared with conjunction search. For this reason, in measurement using a feature search, an error ratio to search time tends to increase. In the inattention measurement system of the present embodiment, since a target time for searching a target is measured by measuring a gazing point of a subject, a more accurate search time can be detected. Learning disability and intellectual disability may occur with ADHD in some cases. Therefore, by combining a conjunction search and a feature search, presence or absence or degree of inattention can be more accurately evaluated.

The imaging unit 120 images the eye of the subject T. The gazing point measurement device 100 may comprise an auxiliary imaging illumination unit. The auxiliary imaging illumination unit radiates near infrared light or visible light to the eye of the subject T. The imaging unit 120 can detect light reflected from the pupil of the subject T and/or light reflected from the cornea, among the light radiated from the auxiliary imaging illumination unit. As a pupil detection method, a conventionally used method such as the method described in Japanese Patent Application Publication No. 2008-125619, for example, can be applied.

The gazing point information measurement unit 131 measures information relating to the history of the gazing point of the subject T by using the image captured by the imaging unit 120. The information relating to the history of the gazing point can include, for example, a direction of line of sight of the subject T and/or a position of the gazing point at each plurality of times within a measurement time. For example, the information relating to the gazing point may include information indicating a time history of line of sight and/or point of sight in a measurement period, or may include a trajectory of point of sight in a measurement period. Information relating to the history of the gazing point may be in the form of numerical data or image data.

The gazing point information measurement unit 131 can comprise a line of sight detection unit that detects line of sight of a subject using a captured image, and a gazing point detection unit that detects a gazing point of the subject using the detected line of sight. As a method of measuring information relating to the gazing point of the subject T by the gazing point information measurement unit 131, a known method such as a method described in Japanese Patent Application Publication No. 2005-198743 can be applied.

The gazing point measurement device 100 of the present embodiment can comprise a storage unit 140. The storage unit 140 may comprise, for example, a nonvolatile memory, a hard disk, a CD-ROM, or the like. The storage unit 140 may be built in or may be detachable from the gazing point measurement device 100. For example, the storage unit 140 can store image data to be displayed on the display unit 110. The storage unit 140 may not store an image to be displayed on the display unit 110. For example, the display unit 110 may display an image based on data of the image supplied via a network.

A control unit 130 of the gazing point measurement device 100 comprises, for example, a processor including a memory such as a RAM and a CPU. The control unit 130 executes various controls and various calculation processes in accordance with a program stored in the storage unit 140, for example, and can function as the gazing point information measurement unit 131. The control unit 130 can be connected to an external device, Internet line or the like via various interfaces (not shown). The control unit 130 may be connected to an input device such as a keyboard and a mouse, or to a communication device to which data can be input from an external device.

The gazing point measurement device 100 may measure a gazing point of a subject. Therefore, the gazing point measurement device 100 is not limited to the above-mentioned device, and other commercially available and well-known devices may be used. For example, one or more of GezeFinder manufactured by JVC Kenwood Corp., gazing point tracking system manufactured by ISCAN, Inc, eye tracking system manufactured by Tobii AB, and device described in Japanese Patent Application Publication No. 2013-052116 may be used. The gazing point measurement device may not comprise the imaging unit 120. For example, the gazing point measurement device may comprise an electrode unit that is attached to the head of a subject and detects movement of the eyeball of the subject, instead of the imaging unit.

Further, techniques described in, for example, Japanese Patent No. 4517049, Japanese Patent No. 4452835, Japanese Patent No. 4452836, Japanese Patent No. 4491604, Japanese Patent No. 4528980 may be applied to the gazing point measurement device of the present embodiment. As a result, the gazing point measurement device can accurately detect the information relating to the gazing point of the subject.

In the gazing point measurement device 100 described above, the visual stimulus 111 is displayed on the display unit 110. However, the visual stimulus 111 may be presented to the subject by slide imaging, storytelling with pictures or the like without using the display unit 110. The visual stimulus 111 may not be displayed as an image as described above. The visual stimulus 111 may be presented to the subject by displaying a three-dimensional object such as diorama.

Upon presenting the visual stimulus 111, a target may be presented to the subject in advance and the subject may be instructed to search for the target. Alternatively, a target may not be presented to a subject in advance, so that the subject may spontaneously direct attention to the target. The gazing point measurement device 100 may comprise a speaker. The speaker can function as a voice output unit that provides instructions or cautions to a subject by voice.

Next, the inattention measurement device 200 of the present embodiment will be described.

For example, the inattention measurement device 200 of the present embodiment comprises an index value calculation unit 211, a threshold comparison unit 212, and a storage unit 220. Based on information relating to a history of a gazing point of a subject measured by the gazing point measurement device 100, the inattention measurement device 200 can calculate an index value indicating the inattention level of the subject (hereinafter referred to as "index value of inattention level") by the index value calculation unit 211. The inattention measurement device 200 can compare the calculated index value with one or more thresholds by the threshold comparison unit 212 to perform inattention measurement.

The index value calculation unit 211 can use, for example, a time (hereinafter referred to as "search time") until the gazing point is detected in a predetermined area including the target (hereinafter referred to as "target area"), so as to calculate the index value of inattention level. The search time indicates a time from when the subject starts searching for the target until when the subject finds the target. The index value of inattention level may be the same value as the search time or may be a value calculated from a single or a plurality of search time by means of a predetermined function (e.g., a linear function or a nonlinear function). For example, the index value of inattention level may be a value calculated using a plurality of search time corresponding to a respective plurality of tasks (for example, cumulative search time, average search time, etc.) The index value of inattention level may be a value obtained by comparing the search time among a plurality of tasks.

The search time can be, for example, a time from when a task is displayed until when the gazing point is detected at least once in the target area. The search time may be a time until the gazing point is detected more than once in the target area. In this case, it is possible to reduce the possibility of erroneously detecting that the problem has been solved by the subject's point of sight being accidentally led the target area. A cycle for detecting the gazing point is, for example, 1/50 seconds, but is not particularly limited.

The target area can be set in accordance with characteristics of the target. For example, when the target is a circle, the target area may be set in a region inside the circle, or may be set in a region within a range obtained by adding a predetermined length to a circle radius from the center of the circle. When the target and the distractor are located close to each other, the target area may be set to a region excluding the distractor from these regions. The target area may be defined by a line connecting a group of points in which a ratio between the shortest distance to an outer periphery of the target and the shortest distance to an outer periphery of the adjacent distractor is a predetermined ratio. For example, a point on the outer periphery of the target area may be set to a position where a ratio between distances from this point to each outer periphery of the nearest target and distractor is a predetermined value (e.g., 1:1).

For tasks with a large number of visual stimuli, the subject (e.g., ADHD child/person) may not be able to find a target. In this case, the search time can be set to a time during which measurement of the gazing point has been conducted (hereinafter referred to as "gazing point measurement time"). The gazing point measurement time can be, for example, a time from when the target is presented until measurement of the gazing point is completed.

For example, the index value calculation unit 211 can calculate the index value of inattention level, using a movement distance of the gazing point (for example, a length of trajectory) within a predetermined time (for example, the search time or the measurement time of the gazing point). The index value of inattention level may be the same as the movement distance or may be a value calculated from one or a plurality of movement distances by means of a predetermined function (e.g., a linear function and a nonlinear function). For example, the index value of inattention level may be a value calculated using a plurality of movement distances corresponding to a respective plurality of tasks (e.g., total distance moved, average movement distance, etc.) The index value of inattention level may be a value obtained by comparing the movement distances between a plurality of tasks. For example, if a subject cannot find the target during the measurement time of the gazing point, the index value of inattention level can be calculated without using the search time. Then, it is possible to evaluate a subject with severe inattention.

The movement distance can be, for example, a total distance moved of the gazing point of the subject within the search time or the measurement time. The total distance moved is calculated, for example, by detecting the gazing point at a predetermined cycle and interpolate the result to find a trajectory of the gazing point. The cycle for detecting the gazing point is, for example, $1/50$ seconds, but is not particularly limited. A measurement start time point and end time point of the movement distance may be appropriately changed depending on a task used.

The index value calculation unit 211 can calculate the index value of inattention level, for example, using number of searches for distractor. The number of searches for distractor is number of times the gazing point of the subject is continuously detected over a predetermined time in a predetermined area including a distractor (hereinafter, also referred to as "distractor area"). The range of the distractor area, as well as the target area described above, can be appropriately defined. The index value of inattention level may be the same as the number of searches for distractor, or may be a value calculated by a predetermined function (e.g., a linear function or a nonlinear function) from the number of searches for one or more distractors. For example, the index value of inattention level may be a value calculated using a plurality of the number of searches for distractor corresponding to a respective plurality of tasks (e.g., total number of searches for distractor, average number of searches for distractor). The index value of inattention level may be a value obtained by comparing the number of searches for distractor among multiple tasks.

The number of searches for distractor can be, for example, number of distractor areas (total number of distractor areas) where the gazing point is continuously detected over a predetermined time during the measurement time of the gazing point. The number of searches for distractor may be number of times the trajectory of the gazing point passing through the distractor area. A measurement start time point and end time point of the movement distance may be appropriately changed depending on a task to be used.

The index value of inattention level may be calculated using only one, or using two or more out of the information relating to the history of the gazing point (e.g., the search time, movement distance and number of searches for distractor). For example, the index value of inattention level may be a value calculated by weighing at least one value of the search time, movement distance and number of searches for distractor in accordance with the information relating to the subject (e.g., age, gender and/or symptoms). The index value of inattention level may be a value calculated using two or more values of the search time, movement distance, and number of searches for distractor, for example, with weighing or the like. For example, items such as a movement pattern of the gazing point may be used for calculation of the index value of inattention level, other than the search time, movement distance and number of distractor areas described in the above. The calculated value may be corrected according to the number of target or distractor.

Depending on the purpose of measuring inattention level, measurement items to be used as the index value of inattention level (search time, movement distance, number of searches for distractor, etc.) may be selected as appropriate. For example, depending on types of tasks, any one or more measurement items of the search time, movement distance and number of searches for distractor may be selected and used as the index value of inattention level, as appropriate. Thereby, measurement of inattention level can be more accurately made.

The threshold comparison unit 212 can make measurement of inattention by comparing the index value of inattention level calculated by the index value calculation unit 211 with one or more thresholds. For example, a relationship between the information relating to the history of the gazing point and the index value of inattention level is set such that the more serious the inattention level is, the greater the index value of inattention level is. The threshold comparison unit 212, if the index value of inattention level is equal to or higher than a threshold, can determine that the subject has inattention symptoms. The threshold comparison unit 212, if the index value of inattention level is less than a threshold, can determine that the subject has no inattention symptoms. By setting two or more thresholds, the degree of inattention symptoms can be also measured.

A threshold is set, for example, based on the index value of inattention level in a subject who has already been diagnosed as inattentive. For example, if a threshold is set according to an index value of inattention level of a typically developing child/person and/or a child/person diagnosed with ADHD, a determination result useful for diagnosis is obtained by the threshold comparison unit 212. Further, a threshold can be set according to a value of a child/person diagnosed with neuropsychiatric diseases other than ADHD. For example, by setting a threshold for each subject according to an index value of inattention level of each subject measured in advance, inattention level of each subject can also be measured under various circumstances (for example, after a long period of work).

The inattention measurement device 200 as described above is realized, for example, by causing a commercially available personal computer to perform a predetermined process. The inattention measurement device 200 comprises a calculation unit 210 and a storage unit 220. The storage unit 220, for example, can include at least one of a non-volatile memory, a hard disk and a CD-ROM. The storage unit 220 can store information relating to a gazing point of a subject acquired by the gazing point measurement device 100, a program for calculating an index value, information relating to a threshold, etc. The storage unit 220 may be incorporated in the inattention measurement device 200, or may be removable from the inattention measurement device 200. The inattention measurement device 200 may not include a storage unit. In this case, for example, the inattention measurement device 200 may commonly use the storage unit 140 of the gazing point measurement device 100. The inattention measurement device 200 may cause the display unit 110 to display a calculation result of the index value of inattention level, or cause a printing medium such as a printer to output the calculation result.

The calculation unit 210 comprises, for example, a memory such as a RAM, and a processor including a CPU. The calculation unit 210, in accordance with the program stored in the storage unit 220, performs various types of processing. This program can be a program for causing a computer to execute calculation of an index value indicating an inattention level of a subject on the basis of information relating to a gazing point of the subject when presented with a certain visual stimulus. The calculation unit 210, by executing a program, can serve as an index value calculation unit 211 and a threshold comparison unit 212. The calculation unit 210 may be connected to an external device, Internet or the like via various interfaces. To the calculation unit 210, input devices such as a keyboard, mouse, etc. may be connected. A communication device through which data can be input from an external device may be connected to the calculation unit 210.

The inattention measurement system 1 of the present embodiment calculates an index value that indicates inattention level, for example, using one or more of the search time, movement distance and number of searches for distractor described above, based on information relating to a history of a gazing point of a subject. Therefore, the inattention measurement system 1 can objectively perform measurement of inattention without the need of the subject's operation of pressing a button. Therefore, measurement of inattention can be performed more conveniently, accurately and objectively even to a subject of preschool age group or severe ADHD child/person who has difficulty to understand contents of a task. The inattention measurement system 1 can make diagnostically useful determination by comparing an index value of inattention level with a threshold.

In the inattention measurement system 1 of the present embodiment, the inattention measurement device 200 may be incorporated into the gazing point measurement device 100, and vice versa. Like a commercial available display integrated computer, the gazing point measurement device 100 or inattention measurement device 200 can also be accommodated in the display unit.

Figure 11:
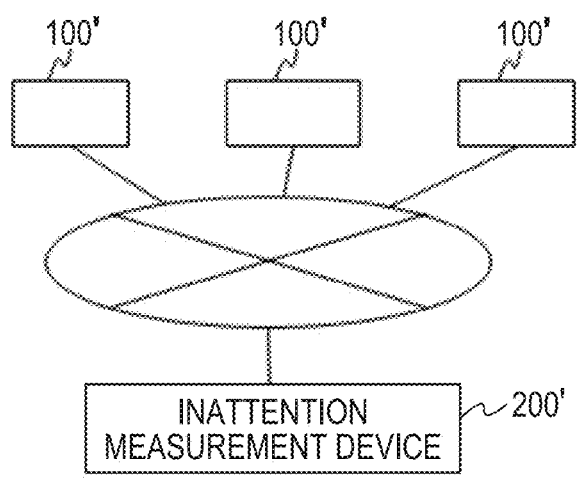
FIG. 11 is a diagram showing an example of the inattention measurement system.

In the inattention measurement system of this embodiment, the gazing point measurement device and the inattention measurement device may not be disposed physically close to each other. For example, as shown in FIG. 11, a gazing point measurement device 100' and an inattention measurement device 200' may be connected via a network including Internet or WAN, LAN, and a communication line such as a dedicated line. Specifically, in facilities such as hospitals at a plurality of locations across the country, information relating to gazing points of a plurality of subjects acquired using the gazing point measurement device 100' can be collected via the network, to perform measurement of inattention.

The inattention measurement device 200 of the present embodiment may not comprise the gazing point measurement device 100. In this case, information acquired in advance by a gazing point measurement device stored in a storage device or the like can be used as information relating to a history of a gazing point of a subject.

Figure 9:
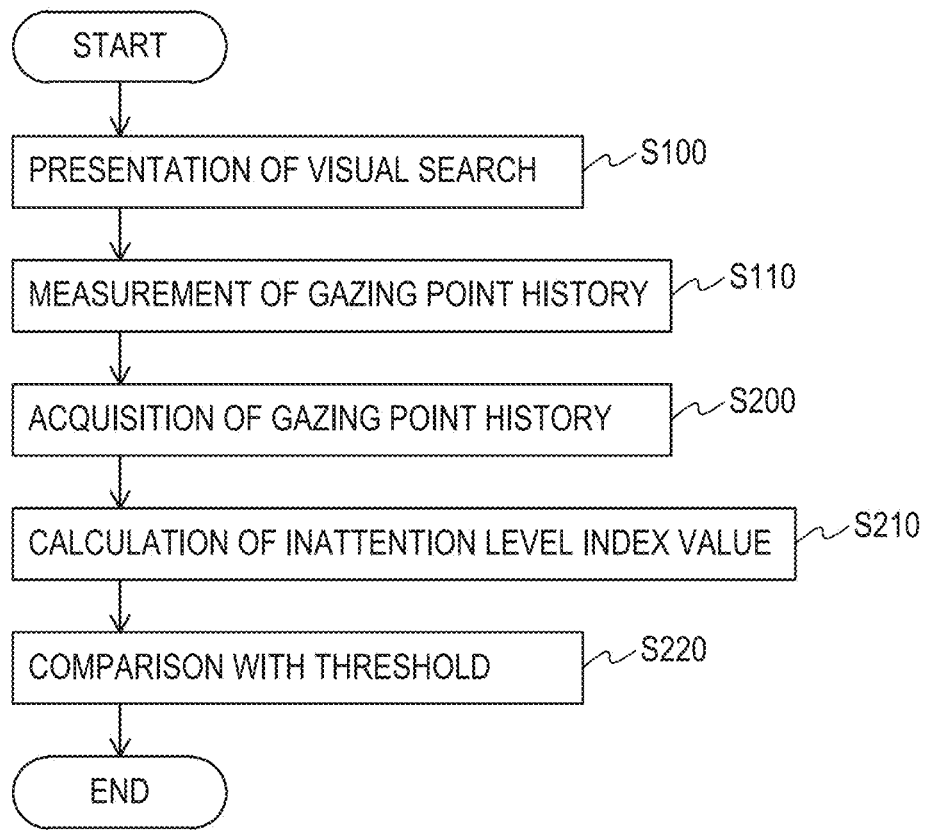
FIG. 9 is a diagram showing an example of a flowchart relating to the inattention measurement system.
Figure 10:
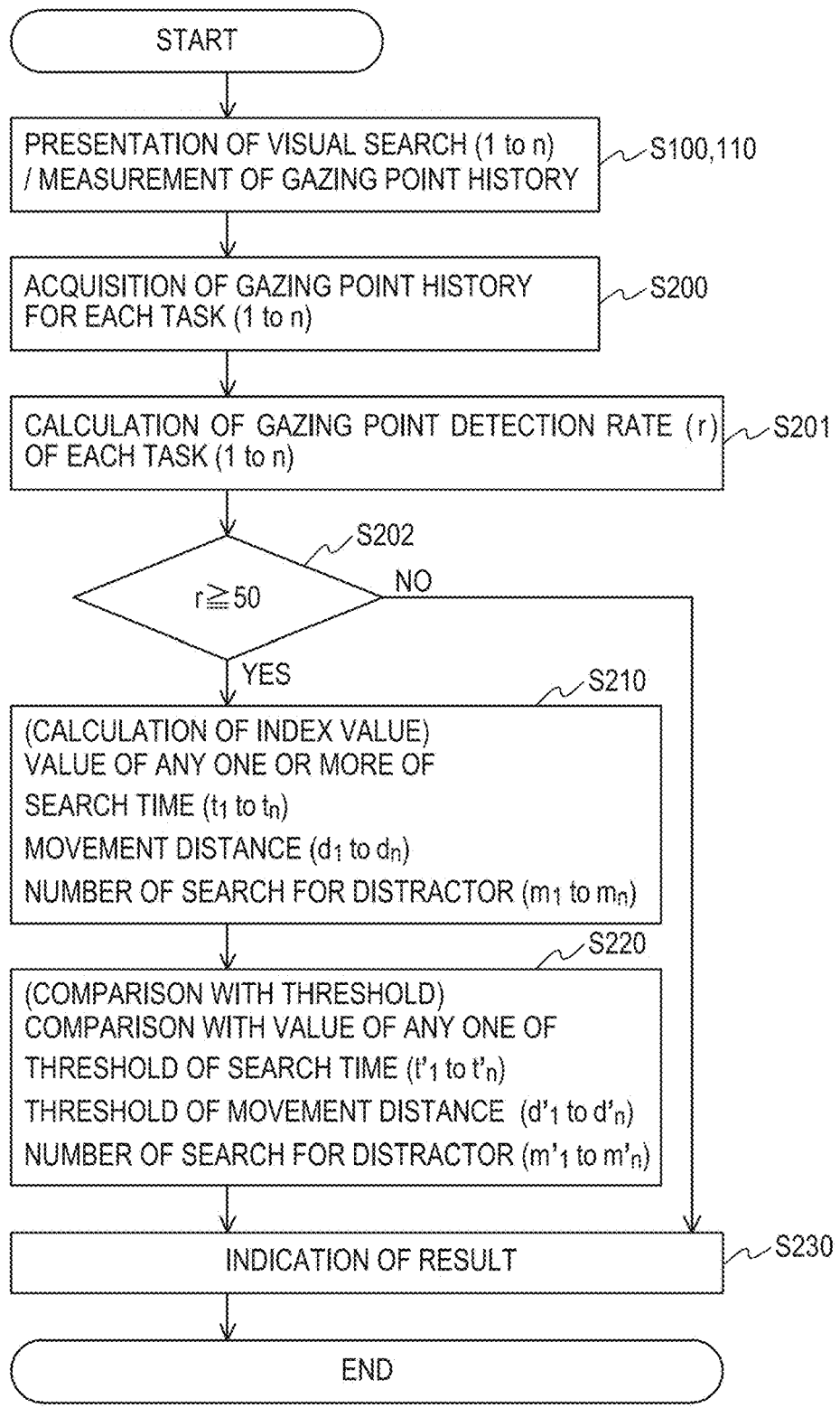
FIG. 10 is a diagram showing an example of a flowchart relating to the inattention measurement system.

FIGS. 9 and 10 are flowcharts showing examples of a process flow in the inattention measurement system. In the inattention measurement system, first, the gazing point measurement device 100 presents a task (visual search) that includes a predetermined target to a subject (S100), and measures information relating to a history of a gazing point of the subject (S110). Next, the inattention measurement device 200 acquires information relating to the history of the gazing point (S200), and calculates an index value of inattention level (S210).

As shown in FIG. 10, if a gazing point detection rate (r, unit: %) (corresponding to data rate in FIG. 6) showing a rate of the gazing point detected on the display unit within the measurement time of each task is a predetermined value or less (e.g., 50%), it may be determined that information relating to the history of the gazing point for calculating an index value of inattention level is not sufficiently obtained, and that it is not necessary to calculate the index value of inattention level (S201, 202).

The index value of inattention level can include a value calculated using any one or more of: 1) time until the gazing point is detected in the target area (search time); 2) movement distance within a predetermined time of the gazing point; and 3) number of searches for distractor area the gazing point is detected. When a plurality of visual searches (1 to n) are presented, at least one of: 1) search time ($t_1$ to $t_n$); 2) movement distance ($d_1$ to $d_n$); and 3) number of searches for distractor area ($m_1$ to $m_n$) may be directly used as the index value indicating inattention level (FIG. 10; S210). The index value indicating inattention level may be calculated using a function having these variables (FIG. 10; S210). Use of all items of 1) to 3) above for the index value of inattention level allows more accurate measurement of attention.

Next, the calculated index value of inattention level is compared with one or more thresholds set in advance (S220). That is, by comparing the index value of the calculated inattention level with one or more thresholds, an inattention level is measured. The threshold, as described above, can be set in accordance with inattention of a typically developing child/person and a child/person diagnosed with ADHD, or the index value of previously measured inattention level of a child/person diagnosed with neuropsychiatric diseases other than ADHD.

Using both feature search and conjunction search as visual stimuli, an index value corresponding to each task may be calculated, and the calculated index value may be compared with a threshold set in accordance with each task. When reaction time is measured using a plurality of different tasks in various neuropsychiatric diseases including ADHD, it has been reported that disease specificity is found in a measurement result. By comparing an index value corresponding to each of different tasks and using values of the measurement items of 1) to 3) above with a threshold set in advance, more sensitive and disease-specific measurement of inattention becomes possible.

The initial value of the threshold can be set based on conventional and known literatures or index values calculated in a relatively small population with obvious symptoms. If respective symptoms of any subject based on which the index value is calculated are newly revealed as a result of the measurement of inattention of the present embodiment, it is also possible to use the data additionally to set a new threshold. In this way, the measurement of inattention of the present embodiment is updated from time to time. According to the threshold suitable for each subject, and information relating to tasks and measurement items suitable for the measurement of inattention level, measurement conditions and measurement items can be adjusted as appropriate. Objective inattention level can be measured on a large scale and quickly.

In the present embodiment, a computer may be caused to read and execute a program for calculating an index value that indicates inattention level of a subject based on information relating to a history of a gazing point of the subject when presented with a certain visual stimulus, and thereby functions of the aforementioned inattention measurement devices 100, 100' may be realized. Here, causing a computer to read and execute a program includes installing the program on the computer. The computer may include an OS and hardware of peripheral devices and the like.

The aforementioned program for calculating an index value that indicates inattention level may be recorded on a computer-readable non-transitory recording medium. The computer-readable non-transitory recording medium include a flexible disk, magneto-optical disk, ROM, portable medium, such as a CD-ROM, and storage device such as a hard disk built in a computer. The recording medium also includes an internal or external storage medium accessible from a distribution server to deliver a program.

The embodiment described above is merely an example, and the present disclosure, including the following example can be practiced in a, form variously modified and/or improved based on knowledge of those skilled in the art.

EXAMPLE

Using an inattention measurement system below, measurement of inattention was performed to 184 children at the age of 5 to 6. As a result, each of the search time, movement distance and number of searches for distractor exhibited a correlation with the total number of inattention scores of psychological evaluation scale "ADHD-Rating Scale" that is used for measurement of inattention symptoms. That is, at least any one of the above three items can be used as an index value of inattention level.

Hereinafter, devices, types of tasks, measurement conditions and the like used in this example will be described.

Gazing point measurement device: GazeFinder manufactured by JVC Kenwood Corp. (this device incorporates a NTSC system CCD camera as an imaging unit, and a LED light emitting circuit as a light source unit.)

Display unit: display manufactured by NEC Corp. (model: LCD192VBK, specifications: LCD 19 inches)

Inattention measurement device: desktop PC manufactured by Hewlett-Packard (model: Pavilion Elite HPE)

Figure 3A:
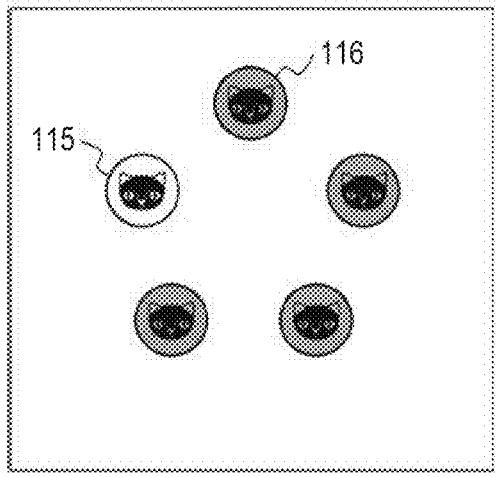
FIGS. 3A to 3F are diagrams each showing an example of feature search and conjunction search.
Figure 3D:
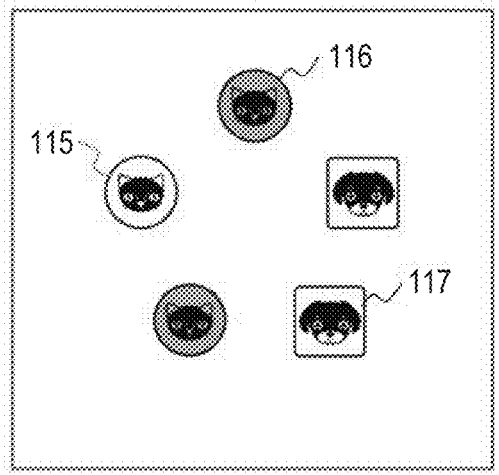
Figure 3B:
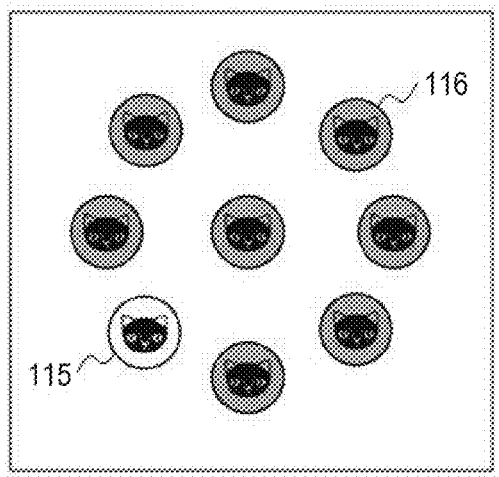
Figure 3E:
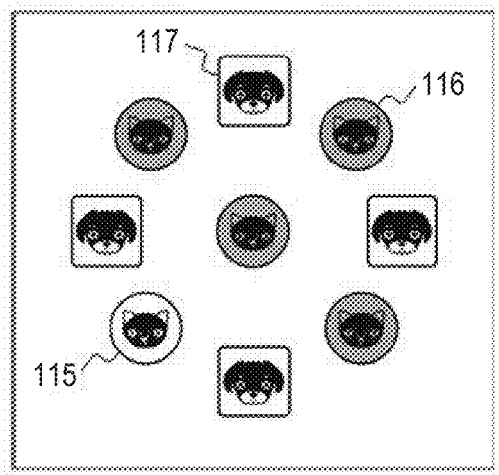
Figure 3C:
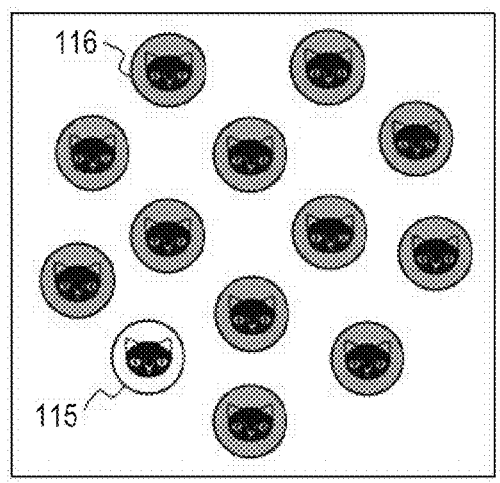
Figure 3F:
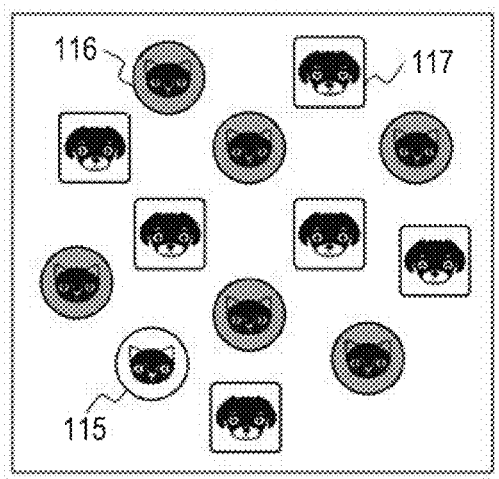

FIGS. 3A to 3F each show an example of feature search (FIGS. 3A to 3C) and conjunction search (FIGS. 3D to 3F) used in this example. In the present example, three types of feature searches are used each including a combination of one target and four, eight, or twelve first distractors of the same shape but different color from that of the target. Below, each of these feature searches is referred to as "feature 4" (example: FIG. 3A), "feature 8" (example: FIG. 3B), and "feature 12" (example: FIG. 3C). In addition, three types of conjunction searches are used respectively including a combination of one target and two, four or six first distractors of the same shape but different color from the target, and two, four or six second distractors of different shape but the same color as the target. Hereinafter, each of these conjunction searches is referred to as "conjunction 4" (example: FIG. 3D), "conjunction 8" (example: FIG. 3E), and "conjunction 12" (example: FIG. 3F).

The target 115 is represented, for example, by a figure of red circle containing a character that mimics a cat. The first distractor 116 is represented, for example, by a figure of blue circle containing a character that mimics a cat. The second distractor 117 is represented, for example, by a figure of red square containing a character that mimics a dog.

Figure 4A:
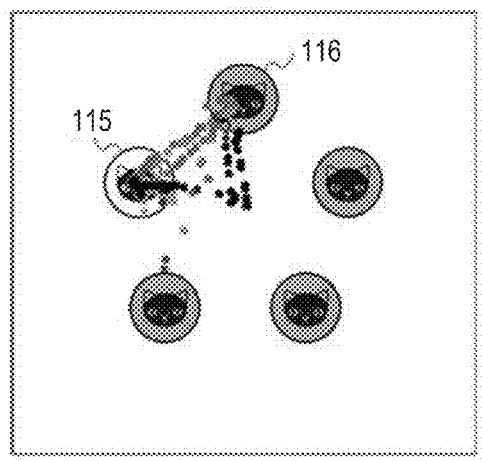
FIGS. 4A and 4B are diagrams respectively showing an example of gazing point positions of a typical developing child and an ADHD child.
Figure 4B:
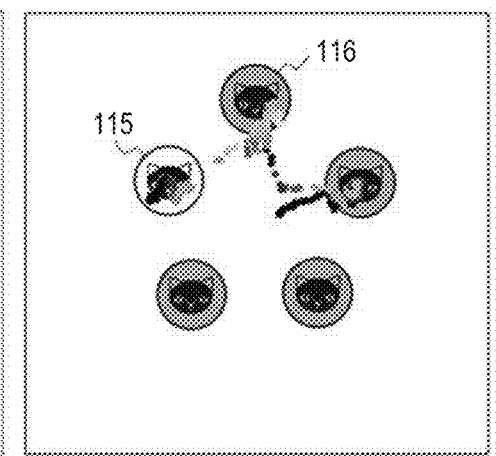

FIGS. 4A and 4B respectively show an example of a plot of every 1/50 seconds of a gazing point of a typically developing child (FIG. 4A) and an ADHD child (FIG. 4B) detected within the measurement time when a feature search is presented on the display unit. In this example, the search time of the target 115 by the typically developing child is 0.220 seconds, while the search time of the target 115 by the ADHD child was 1.300 seconds. The typically developing child can find the target 115 immediately, and tends to look at the target 115 for a longer time than the distractor 116. On the other hand, the ADHD child finds the distractor 116 earlier than the target 115, and tends to look at the distractor 116 for a longer time. In the plot images shown in FIGS. 4A, 4B, 5A and 5B, if positions (coordinates) at which the gazing point is detected overlap, the color of the gazing point may be changed, for example, from "blue to green, to yellow, to orange, and to red" to display the gazing point (heat map display).

FIGS. 5A and 5B respectively show an example of a plot of every 1/50 seconds of a gazing point of a typically developing child (FIG. 5A) and an ADHD child (FIG. 5B) detected within a measurement time when a conjunction search is presented on the display unit. In this example, the search time of the target 115 by the typically developing child is 0.840 seconds, while the search time of the target 115 of the ADHD child was 3.120 seconds. The typically developing child, although temporarily enchanted by one of the distractors 117, continued the search for the target, and then found the target 115 immediately. On the other hand, the ADHD child was enchanted by one of the distractors 117, and could not continue the search for the target. As a result, the search time of the target 115 was much longer.

FIG. 6 shows an example of a result display screen for each measurement item (search time 314, movement distance 315, total number of search for distractor 316) when measurement of inattention was performed.

Figure 7:
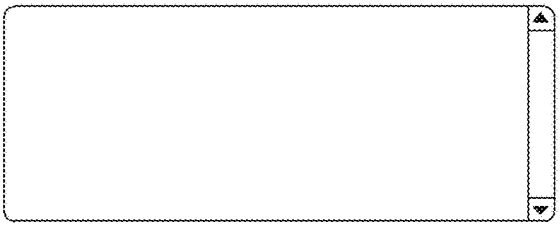
FIG. 7 is a diagram showing an example of information relating to a subject.

FIG. 7 shows an example of a screen that displays information relating to a subject. Each of the measurement items described above is stored in the storage unit in association with the information relating to the subject (age, gender, symptoms and the like), so that it is possible to set a threshold in accordance with various purposes.

Figure 8:
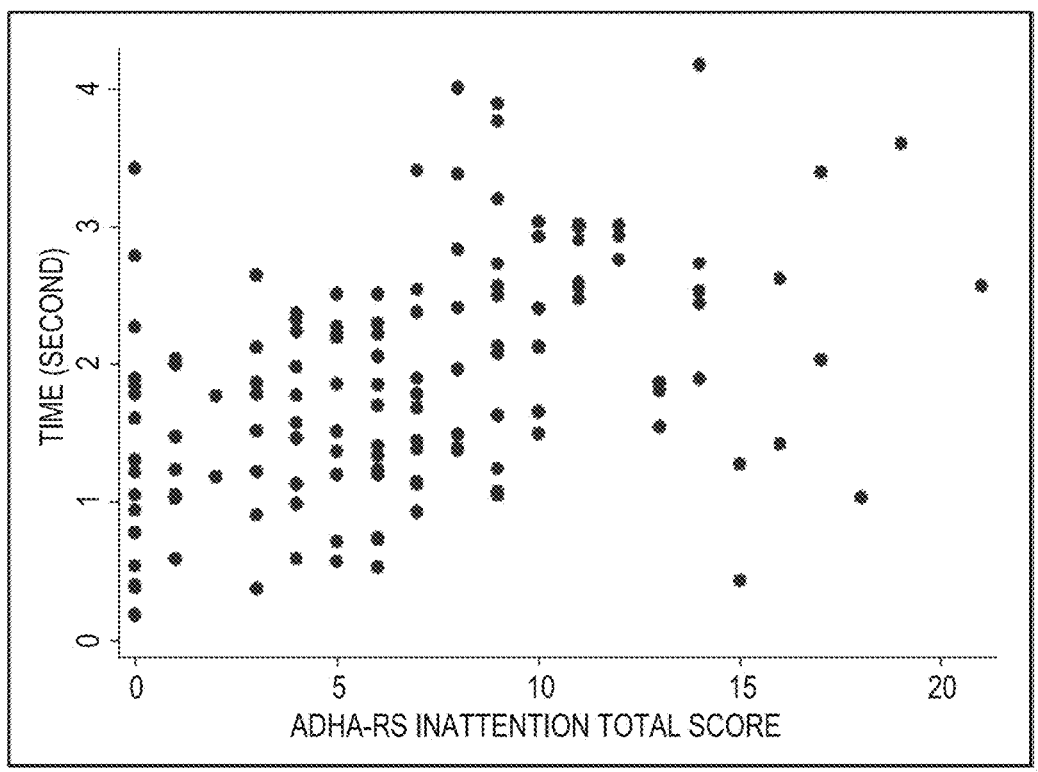
FIG. 8 is a diagram showing a relationship between search time and ADHD evaluation scale/inattention total point.

FIG. 8 shows in a graph a relationship between search time (vertical axis) in conjunction search (conjunction 12, example: FIG. 3F) and ADHD-Rating Scale/inattention total score (horizontal axis), as an example showing a relationship between index value of inattention level and ADHD-Rating Scale/inattention total score, in this example. Correlation is observed between the search time and the ADHD-Rating Scale/inattention total score. When the number of subjects (n) is 184, a correlation coefficient (r) is 0.420 ($p<0.001$).

Hereinafter, an example will be described of an algorithm for determining inattention level by comparison of the index value of inattention level calculated in this example with the threshold.

In this algorithm, when at least one condition of the following cases 1) to 3) is satisfied, it is determined that inattention is present. As shown in FIG. 10, when the gazing point detection rate (r) is less than 0.5, the determination of presence or absence of inattention is not performed.

1) In a case where any of the feature searches (feature 4, feature 8, feature 12) is displayed, the search time is 1.5 seconds or more, or the movement distance without successful search for the target is 1000 pixels or more.

2) In "conjunction 12", the search time is more than 3 seconds, or the movement distance without successful search for the target is 2000 pixels or more.

3) In "conjunction 8", the search time is 2.5 seconds or more, or the movement distance without successful search for the target is 2000 pixels or more, and, in "conjunction 12", the time search is 1.5 seconds or more.

As described above, by combining the feature search and the conjunction search, and using the search time and the movement distance as the index value of inattention level, the index value is compared with a threshold set for each task. Thereby, the determination of inattention equivalent to the ADHD-Rating Scale can be made. The value of which item should be the index value of inattention level can be appropriately determined in consideration of a measurement object, a subject to be determined, or accuracy to be requested, of inattention level. The index value indicating inattention level (value of each measurement item) or the threshold can be corrected or adjusted, as appropriate, depending on the age, gender, etc. of the subject to be determined.

The technical scope of the present invention is not limited to the above example. Further, the algorithm upon performing the determination of inattention level can be set as appropriate according to the subject and the task to be used.

Use of the inattention measurement device, system, inattention level measurement method and the like of the present disclosure can support clinical evaluation of inattention and diagnosis of attention deficit. Especially for ADHD of low age group, early detection and early diagnosis of inattention can be made based on objective assessment. Further, not only in medical fields but also under various circumstances (for example, after a long period of work), measurement of inattention level of each individual can be performed simply, accurately and objectively.

The invention claimed:

1. An inattention measurement system comprising:
   a gazing point measurement device that measures information relating to a history of a gazing point of a subject when presented with a task of searching for a predetermined target in a visual search including the target and a distractor; and
   an inattention measurement device that calculates an index value indicating an inattention level of the subject based on the information relating to the history of the gazing point measured by the gazing point measurement device,
   wherein the index value indicating the inattention level of the subject includes at least one of:
      a value calculated using a movement distance within a predetermined time of the gazing point, or
      a value calculated using a number of times the gazing point is detected in a predetermined area including the distractor.

2. The inattention measurement system according to claim 1,
   wherein the visual search includes a conjunction search.

3. The inattention measurement system according to claim 1,
   wherein the visual search includes a feature search.

4. The inattention measurement system according to claim 1, wherein the inattention measurement device compares the calculated index value indicating the inattention level of the subject with one or more thresholds set in advance.

5. The inattention measurement system according to claim 4,
   wherein at least one of the one or more thresholds is set according to the index value indicating the inattention level calculated for a given subject.

6. The inattention measurement system according to claim 5,
   wherein the given subject is selected from the group consisting of: a typically developing person and patients diagnosed with attention deficit/hyperactivity disorder.

7. The inattention measurement system according to claim 6,
   wherein the given subject is selected from the group consisting of: a typically developing person, patients diagnosed with attention deficit/hyperactivity disorder, and a patient diagnosed with at least one neuropsychiatric disease other than attention deficit/hyperactivity disorder.

8. The inattention measurement system according to claim 1,
   wherein the index value indicating the inattention level of the subject includes at least two or more of:
      a value calculated using a time until the gazing point of the subject is detected in a predetermined area including the target;
      a value calculated using the movement distance within a predetermined time of the gazing point, or
      a value calculated using the number of times the gazing point is detected in a predetermined area including the distractor.

9. The inattention measurement system according to claim 1,
   wherein the index value indicating the inattention level of the subject includes:
      a value calculated using a search time of a target until the gazing point of the subject is detected in a predetermined area including the target;
      a value calculated using the movement distance, or
      a value calculated using the number of times.

10. An inattention level measurement method comprising:
    calculating an index value indicating an inattention level of a subject based on information relating to a history of a gazing point of the subject when presented with a task of searching for a predetermined target in a visual search including the target and a distractor; and
    comparing the index value indicating the calculated inattention level of the subject with one or more thresholds set in advance,
    wherein the index value indicating the inattention level of the subject includes at least one of:
       a value calculated using a movement distance within a predetermined time of the gazing point, or
       a value calculated using a number of times the gazing point is detected in a predetermined area including the distractor.

11. A non-transitory computer-readable recording medium storing computer executable instructions for causing a processor to perform the method according to claim 10.

12. An inattention measurement system, comprising:
    an index value calculator; and
    a non-transitory computer-readable recoding medium storing computer executable instructions that causes one or more processors, when performed by the one or more processors, to perform a step including:
       receiving information relating to a history of a gazing point of a subject when presented with a task of searching for a predetermined target in a visual search including the target and a distractor; and
       calculating an index value relating to an inattention level of the subject based on information relating to a history of the gazing point,
    wherein the index value is calculated based at least partially on at least one of:
       a movement distance within a predetermined time of the gazing point; or
       a number of times the gazing point is detected in a predetermined area including the distractor.

13. The inattention measurement system according to claim 12, wherein the visual search includes a feature search and a conjunction search, wherein the calculating the index value includes:

calculating a first index value with respect to the feature search; and calculating a second index value with respect to the conjunction search.

14. The inattention measurement system according to claim 12, wherein the index value is calculated based at least partially on at least one of the movement distance or the number of times, and the search time of the target until the gazing point of the subject is detected in a predetermined area including the target.

15. The inattention measurement system according to claim 12, wherein the index value is calculated based at least partially on the movement distance and the number of times.

16. The inattention measurement system according to claim 12, wherein the index value is calculated based at least partially on the movement distance, the number of times, and the search time of the target until the gazing point of the subject is detected in a predetermined area including the target.

17. The inattention measurement system according to claim 12, wherein the receiving the information relating to the history of the gazing point includes:

presenting the visual search to the subject;

obtaining the information relating to the history of the gazing point; and calculating a gazing point detection rate with respect to the visual search based on the information relating to the history of the gazing point.

18. The inattention measurement system according to claim 17, wherein the calculating the index value includes:

calculating the index value based at least partially on the movement distance on condition that the gazing point detection rate is greater than a first threshold;

comparing the calculated index value with a second threshold; and displaying a result of the comparison.

19. The inattention measurement system according to claim 17, wherein the calculating the index value includes:

calculating the index value based at least partially on the number of times on condition that the gazing point detection rate is greater than a first threshold;

comparing the calculated index value with a second threshold; and displaying a result of the comparison.

20. The inattention measurement system according to claim 17, wherein the calculating the index value includes:

calculating the index value based at least partially on at least one of the movement distance or the number of times, and a time until the gazing point of the subject is detected in a predetermined area including the target on condition that the gazing point detection rate is greater than a first threshold;

comparing the calculated index value with a second threshold; and displaying a result of the comparison.

* * * * *